United States Patent
Wrobel (10) Patent No.: US 7,878,062 B2
(45) Date of Patent: Feb. 1, 2011

(54) ADVANCED ULTRASONIC INTERFEROMETER AND METHOD OF NON-LINEAR CLASSIFICATION AND IDENTIFICATION OF MATTER USING SAME

(75) Inventor: Miroslaw Wrobel, Toronto (CA)

(73) Assignee: Nimtech Inc., Charlottetown, PEI (CA)

( * ) Notice: Subject to any disclaimer, the term of this patent is extended or adjusted under 35 U.S.C. 154(b) by 535 days.

(21) Appl. No.: 11/993,211

(22) PCT Filed: Jun. 27, 2006

(86) PCT No.: PCT/CA2006/001062

§ 371 (c)(1),
(2), (4) Date: Dec. 19, 2007

(87) PCT Pub. No.: WO2007/000047

PCT Pub. Date: Jan. 4, 2007

(65) Prior Publication Data

US 2010/0132468 A1    Jun. 3, 2010

(30) Foreign Application Priority Data

Jun. 28, 2005    (CA)    ................................. 2510972

(51) Int. Cl.
*G01N 29/12*    (2006.01)
*A61B 8/00*    (2006.01)
*G01N 29/50*    (2006.01)

(52) U.S. Cl. ............................ 73/579; 73/602; 600/439

(58) Field of Classification Search .................. 73/579, 73/597, 598, 599, 600, 602, 19.03, 24.01, 73/24.05, 32 A, 54.41, 61.49, 61.45, 61.79, 73/64.53; 600/439; 601/2–4

See application file for complete search history.

(56) References Cited

U.S. PATENT DOCUMENTS

| 3,952,578 A | * | 4/1976 | Jacobs ........................ 73/64.42 |
| 4,648,276 A | * | 3/1987 | Klepper et al. ................. 73/599 |
| 5,724,138 A | * | 3/1998 | Reich et al. .................. 356/492 |

(Continued)

FOREIGN PATENT DOCUMENTS

WO    WO2005/009244 A1    2/2005

OTHER PUBLICATIONS

"Measurement of Harmonic Signal Phase with Application of Low Frequency of Sampling", Leon Jodlowski, Molecular and Quantum Acoustics, 1998, vol. 19, p. 111-119, ISSN 0208-5151.

(Continued)

*Primary Examiner*—Hezron Williams
*Assistant Examiner*—Rose M Miller
(74) *Attorney, Agent, or Firm*—Lang Michener LLP (57) ABSTRACT

An ultrasonic interferometer for the characterization of the matter (solids, fluids & gases) in a medium is described, along with a method of using the same. The interferometer accurately determines the travel time of the multi-frequency ultrasonic signal in the matter that is being queried. By carefully selecting the design of the multi-frequency ultrasound signal, various properties of the material can be derived using a trainable classification system to classify or recognise the substance, or state of a process. The apparatus exploits the normally undesirable higher harmonics characteristics of the piezoceramic transducer to gain penetration through a spatial-frequency window that is not suitable for the higher frequency signals that are required to achieve the measurements.

12 Claims, 10 Drawing Sheets

U.S. PATENT DOCUMENTS

| | | | |
|---|---|---|---|
| 6,378,357 B1* | 4/2002 | Han et al. | 73/54.41 |
| 2003/0167848 A1 | 9/2003 | Glaser et al. | |
| 2003/0171677 A1* | 9/2003 | Marmarelis | 600/441 |
| 2004/0006436 A1* | 1/2004 | Morgen et al. | 702/48 |
| 2004/0065143 A1* | 4/2004 | Husher | 73/64.53 |
| 2004/0087860 A1* | 5/2004 | Lee et al. | 600/468 |
| 2005/0033171 A1 | 2/2005 | Stergiopoulos et al. | |

OTHER PUBLICATIONS

"Pomiar zmian predkosci fazowej w cieczy z zsatosowaniem cyfrowego przetwarzania zygnalu", Szustakowski M., et al., Molecular and Quantum Acoustics, 1998, vol. 19, p. 271-281, ISSN 0208-5151.

"Analysis of Measurement Possibilities of Long Bulk Wave for Technical Application", Leon Jodlowski et al., Molecular and Quantum Acoustics, 1999, vol. 20, p. 103-109, ISSN 0208-5151 .

"Passage Time Measurement of Medium Probe Signal with the Use of Phase Method with Quasi-Continuous Wave", Szustakowski M., et al., Molecular and Quantum Acoustics, 1999, vol. 20, p. 279-291, ISSN 0208-5151.

"Accurate Distance Measurement by an Autonomous Ultrasonic System Combining Time-of-Flight and Phase-Shift Methods", Francis Gueuning et al., IEEE Transactions on Instrumentation and Measurement, vol. 46, No. 6, Dec. 1997.

"Analysis of measurement possibilities of acoustic wave packets for technical and medical applications", Mieczyslaw Szustakowski et al., Molecular and Quantum Acoustics, 2000, vol. 21, ISSN 0208-5151.

* cited by examiner

Figure 10

ADVANCED ULTRASONIC INTERFEROMETER AND METHOD OF NON-LINEAR CLASSIFICATION AND IDENTIFICATION OF MATTER USING SAME

FIELD OF THE INVENTION

This invention pertains to the field of automated classification of a substance, or determination of the state of a process. Specifically, it relates to an ultrasonic interferometer and its use in identifying matter or the state of a process.

BACKGROUND OF THE INVENTION

U.S. Pat. No. 5,388,583, issued Feb. 14, 1995 to A. Ragauskas, et al., entitled "Method and Apparatus for Non-Invasively Deriving and Indicating of Dynamic Characteristics of the Human and Animal Intracranial Media", describes a technique that use the phase and higher harmonic characteristics of the transmitted ultrasound signal to measure changes in the brain tissue. This method is based short-pulsed ultrasonic signals and the time measurements are based on the time elapsed between the transmitted signal and the received signal. This elapsed time, together with some phase shift, is used to provide an estimate of the total travel time of the fast-rising short acoustic pulse. This method does not permit an accurate measurement of travel time, density, dispersivity and classification as it uses single estimated travel time and does not consider the cases of multiple frequencies.

German Patent DE 103 24 990 to M. Wrobel, et al., issued Nov. 4, 2004, entitled "Vorrichtung zur Untersuchung eines flüssigen oder gasförmigen Mediums" (Device for the Investigation of a Liquid or Gaseous Media), describes an ultrasonic interferometer. However, the interferometer described therein does not accommodate the concept of multiple frequencies at the same time. It must scroll through multiple frequencies, which prevents it from monitoring fast processes. Furthermore ultrasonic interferometer described therein utilizes the phase of the signal only and cannot overcome the issue of the 360 degree phase shift. Finally, it is not a scalable system, in that the measurements are based on the geometry and characteristics of each individual sensor. This means that the profiles learned from one system cannot be transferred to another system because the sensor characteristics will be different. The system described in German Patent DE 103 24 990 must relearn everything when it is initialized the first time.

German Patent Application DE 100 27 827 to M. Wrobel, et al., filed Jun. 5, 2000, published Dec. 6, 2001 and entitled "Adaptive Klassifikationseinrichtung" (Adaptive Classification Apparatus) is directed towards a classification system for ultrasound FM signals passed through human tissue. The classification system uses a time varying signal spectrum, i.e. a spectrogram, to achieve classification. In the present invention, classification is achieved by measuring travel times.

PCT application WO204/CA01401 to M. Wrobel and S. Stergiopoulos, published Feb. 3, 2005, entitled "Non-Invasive Monitoring of Intracranial Dynamic Effects and Brain Density Fluctuations", describes an ultrasonic interferometer that requires at least two transmitting pulses for its operation. Furthermore, the concept of "beat-frequency phase" as described herein is simply the difference of the phase shifts from two successive transmissions, and is not used as a technique to accurately determine the time from a pair, or pairs of phases. Consequently, it suffers from the cyclic nature of the phases, and cannot differentiate $\phi$ from $(\phi+2\pi)$. Furthermore, it has that shortcoming that the frequency window that can be used is limited by the thickness of the skull bone. Furthermore, the classification is based solely on the difference of the two phases.

SUMMARY OF THE INVENTION

This invention impacts the area of quality control, process control, medical diagnosis and material classification. Ultrasonic signals are well known to penetrate various types of materials, and tissues. It is primarily used in imaging application because of this property. Based on this property the present invention allows for the classification of matter in closed containers as well as open systems. This provides a number of benefits; it is possible to query the brain matter through the temporal bone; it is possible to query a fluid in a closed bottle vat; it is possible to query a fluid or gas as it flows through a pipeline.

The invention uses a multi-frequency coded ultrasonic signal to gather all of the information that is needed to characterize the substance that makes up the medium. The phase of each of the frequencies in the coded multi-frequency signal is determined using conventional techniques, and these phases in various combinations provide measurements of the travel times of the particular frequencies. Based on this information, the density, the bulk modulus, the speed of sound and the time of flight of the continuous signal in the medium can be characterized.

The natural, usually non-desirable, higher harmonic property of ultrasonic piezoceramic transducers is also exploited by this invention. Typically. it is impossible to penetrate certain materials or objects with higher frequency ultrasonic signals because the attenuation of these signals is too high. However the higher harmonics are used in this invention to achieve this penetration. By deploying a lower frequency signal, the higher harmonics are also deployed. For materials with small acoustic windows like bones, some plastics or metal-hybrid material—this technique makes it possible to send higher frequencies through this window.

The beating of two frequencies is used to establish a baseline. Any two periodic signals possess a natural common beat period. During one beat period there is no duplication of a phase pair of the two periodic signals. Therefore any valid phase pair can be used to accurately pinpoint a time moment in the beat period. This is used to accurately determine the time of flight of the signal through the medium.

The measurement of the phase parameters and travel times are used to created a profile of the substance. This measured profile is used in a trainable classification system (a non-linear classification system, if necessary) to produce a reliable indication of the substances in the medium. This same classification system is used for detection of changes within the brain such as the detection and classification of strokes, detection of the type of a fluid, determination of the state of a process or the quality of a substance. The system can continuous query the medium and can dynamically track changes in the medium or process.

Each piezoceramic transducer has a tendency to generate the higher harmonics of the produced signal. Normally it is $3^{rd}$, $5^{th}$, $7^{th}$ harmonics and so on. Up to now, this natural property of the transducer has been undesirable and has, typically, been reduced by using filters. This property of the transducers is based on the fact that signal generated by transducer is not of an ideal sinusoidal form. The generated signal is a sinusoid, but also it includes some of the higher harmonics. By using this deficiency of the piezoceramic transducer, the higher frequency signals are also generated. Sending the higher frequencies as a small distortion of the ideal sinusoid enhances these higher harmonics. After receiving the reflection the transmitted signals, the primary frequency as well as the harmonics are known, and the phases can be computed even if there is substantial noise accumulated while travelling through the medium.

The classification of the material is done with the array of travel times computed. The density reference is also available to aid in the classification if it is needed. The classification system requires a reference profile that it will compare the measurements against. This profile is the known profile of the material, substance or state of a process. This profile can be learnt by the processing system or maybe previously known and provide as an input to the system, similar to mass spectrograph. This means that profiles can be shared between these systems. The array of travel times measured by one system can be used in another system to provide a classification or recognition of a substance or process state. The nature of the measurement system makes it dimensionally scalable, which means that the ratio of the travel times would remain the same regardless of the travel distance. This means the classification system would not need to change if the size, shape or geometry of the transmit/receive sensor is changed.

The classification system is completely trainable both online or offline. The profiles required for classification can be generated by the system during use, or downloaded from a database or another system. The technique used to match the measurement against the profiles can be simple (e.g. Euclidean norm) or more complex (e.g. non-linear classification system—such as a multi-layer perceptron neural network). Any form of pattern matching is sufficient for the classification. The vector of travel times that is used to perform the classification can follow a known path as the substance undergoes changes (e.g. in a manufacturing process, or reaction of the human tissue to a medication). This means the actual path of the vector can be previously known and it can be used to track a process continuously. The measurement and classification system will provide dynamic monitoring and/or recognition.

The use of a quasi-constant pulse or a continuous illumination decreases the intensity of the pressure waves in the medium. This is described in Table 1. The parameters of a quasi-constant wave of 50 mW/cm2 (which is the maximum power density allowed by the FDA for medical ultrasound) and frequency of 3 MHz is shown in the left column, and the parameters of a pulsed series of the same intensity and frequency is shown in the right column.

TABLE 1

Comparison of the influence of a constant wave and a pulse series

| Constant Wave | Pulse Series |
| --- | --- |
| Intensity: 50 mW/cm$^2$<br>Frequency: 3 MHz<br>$T_p$ = 200 µs<br>Acoustic Pressure | Intensity: 50 mW/cm$^2$<br>Frequency: 3 MHz<br>$t_i$ = 4 Periods ⇔ 1 Pulse |
| $I = \frac{p_0^2}{2Z}$<br>$Z = 1.48 \times 10^6$ kg/m$^2$s<br>$p_0 = \sqrt{2IZ}$ = 38.5 kPa<br>(Barometric Pressure 101 kPa) | $I_{srti} = \frac{1}{T_p}\int_0^{T_p} \frac{p_0^2}{2Z} dt = \frac{p_0^2}{2Z}\frac{T_p}{t_i}$<br>$p_0 = \sqrt{I2Z\frac{T_p}{t_i}}$ = 471 kPa<br>(More than 4 Times Greater than Barometric Pressure) |
| Average Speed of the Molecules $U_0 = \frac{p_0}{Z}U_0 = \frac{p_0}{Z}$ | |
| 26 mm/s | 318 mm/s |
| Average Deflection of the Molecules $Z_0 = \frac{U_0}{\omega_0}$ | |
| 1.36 nm | 16.9 nm |

Table 1 shows that the pressure introduced to the medium by the pulsed waves is 4 times higher than barometric pressure, whereas the pressure introduced by the quasi-constant signal is about 38% that of barometric pressure. The average speed of the molecules as well as the average molecular displacement is more than 12 times greater with the pulsed signal. This indicates that the pulsed signal is creating significantly more disturbance, and this is not desirable. In some processes, this could alter the state of the medium and change the course of the process. Also the pulsed wave could be more damaging to biological tissue (with a pressure of 4 times that of barometric pressure) than a quasi-constant wave with pressure induced less than barometric pressure.

The present invention provides one or more of the following advantages over the prior art:

Use of a coded multi-frequency signal to investigate various properties of the medium simultaneously and to measure a characteristic profile of the substance. This makes it possible to quickly analyze the substance.

The measurement of an array of travel times that provides the dispersive time characteristics of the medium.

The use of the higher harmonics of the ultrasonic transducers to allow for the penetration of higher frequency ultrasonic signals through a window that is otherwise not suited for high frequency penetration.

The use of multiple phase measurements simultaneously to accurately determine the travel time of signals of different frequencies in the medium.

The measurement and classification system is designed to provide both static and time varying monitoring and/or recognition.

The information from a system based on this invention can be shared with other systems based on this invention, or between the systems and a database, similar to the practice in mass spectrometers.

Other and further advantages and features of the invention will be apparent to those skilled in the art from the following detailed description thereof, taken in conjunction with the accompanying drawings.

BRIEF DESCRIPTION OF THE DRAWINGS

The invention will now be described in more detailed, by way of example only, with reference to the accompanying drawings, in which like numbers refer to like elements, wherein.

DETAILED DESCRIPTION OF THE PREFERRED EMBODIMENTS

Figure 1:
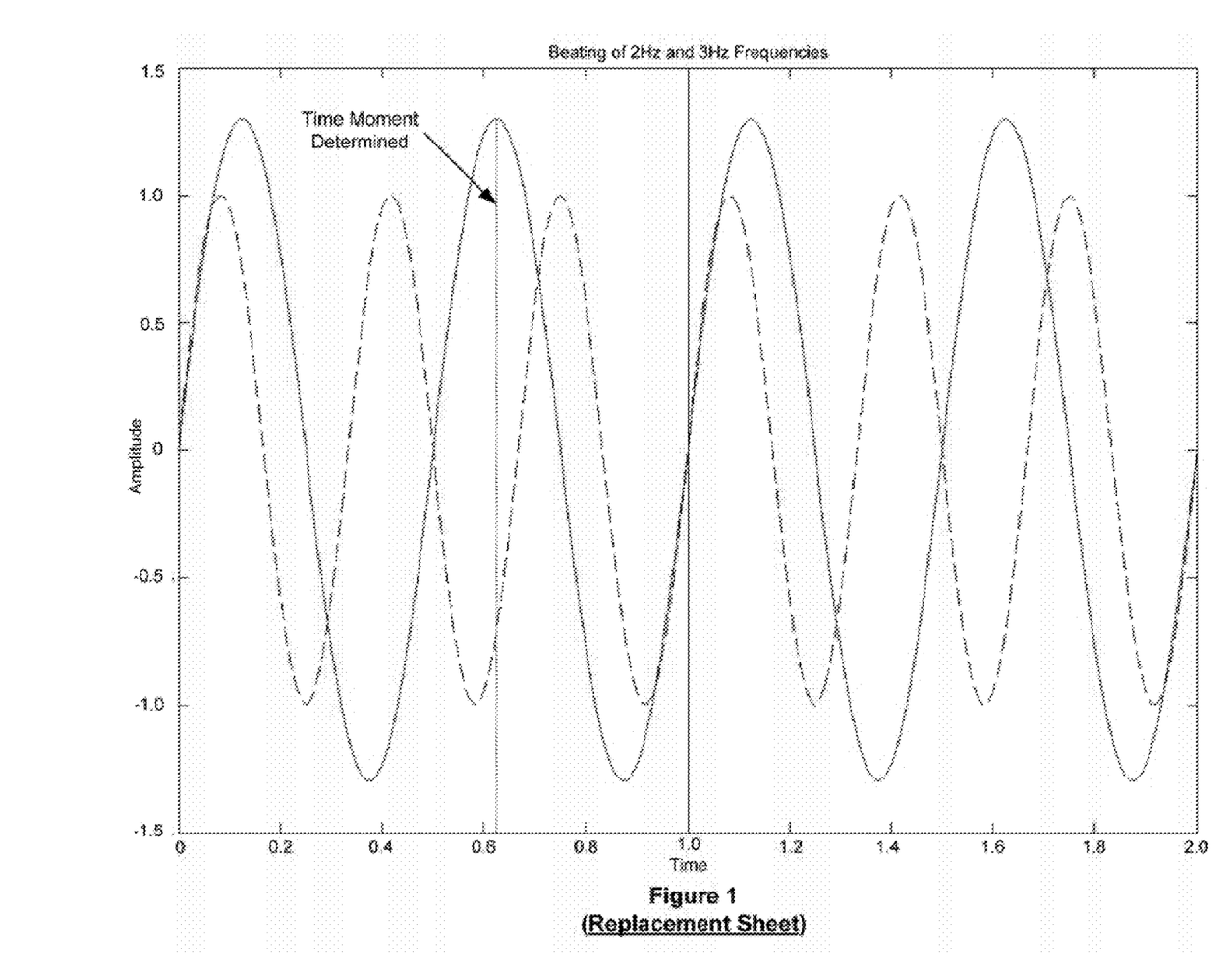
FIG. 1 is a graph showing the beating of two frequencies.

Any two periodic signals exhibit a natural beating frequency. Consider two sinusoidal signals of frequencies $f_1$ and $f_2$. The periods of the two signals are defined by $\tau_1$ and $\tau_2$ respectively. When $$k_1 \tau_1 = \frac{k_1}{f_1} = k_2 \tau_2 = \frac{k_2}{f_2} k_1, k_2 \in N, \qquad (1)$$

is satisfied, with the smallest possible $k_1$ and $k_2$, then $k_1\tau_1$ represents the beat period, with the corresponding beat frequency $1/k_1\tau_1$. FIG. 1 shows this principle. Here two frequencies of $f_1$=2 Hz and $f_2$=3 Hz are shown. From (1) $k_1$=2, and $k_2$=3, including that the beat period is 1 sec, and the beat frequency is 1 Hz. Selecting two frequencies that are close together will result in a long beat period, and hence can measure the travel time for a long distance. The concept of a beating frequency is important because this makes it possible to predict the precise time moment from the two phases. Each of the phases is periodic, which makes it impossible to uniquely identify the time moment. However within the beating period a pair of phases can be used to precisely identify the time moment.

Figure 2:
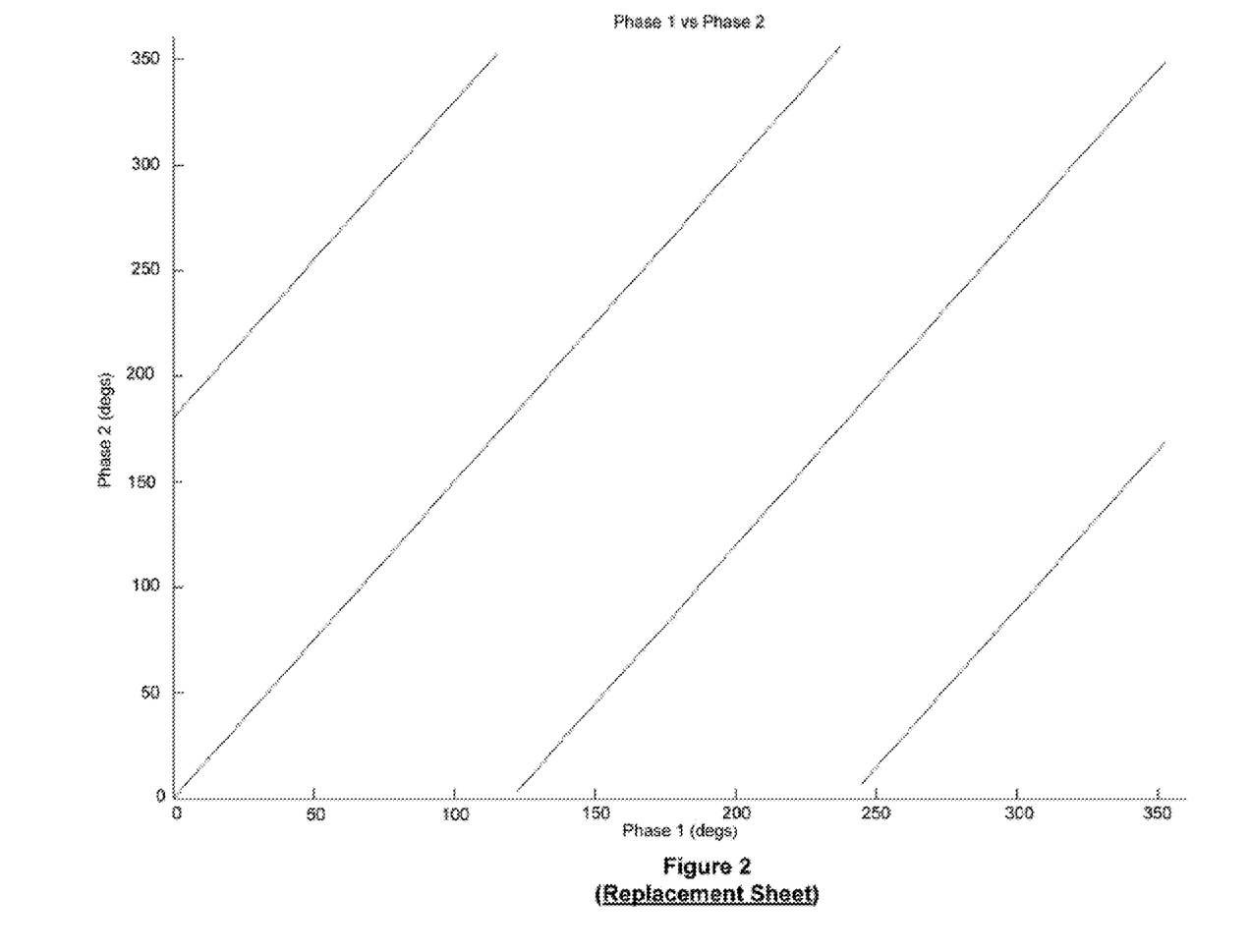
FIG. 2 is a graph of phase relationship between two signals in a beat period.

During this beat period, each time point is characterized by a unique pair of phases of the two frequencies. In the example of two sinusoidal signals, at any time moment the phase of the signal with frequency $f_1$ is given by $(2\pi f_1 t)$ and the phase of the signal frequency $f_2$ is given by $(2\pi f_2 t)$. Considering the phase relationship of $(2\pi+\phi)=\phi$, the plot of FIG. 2 shows the relationship between the phases of the two signals. In this figure the one-one relationship between the phases is evident. The consequence of this is that from any valid pair of phases, the time moment of their occurrence can be uniquely determined. FIGS. 1 and 2 depict and example where the phase pair of (90°, 135°) is measured (90° on the curve shown with the solid line and 135° on the curve shown with the dashed line). This location is marked in FIG. 2. The combination of these two phases map to one unique location in the beat period, as is marked in FIG. 1. This time shown by the dotted vertical line is the only time moment within the beat period that this pair of phases can occur.

Figure 3:
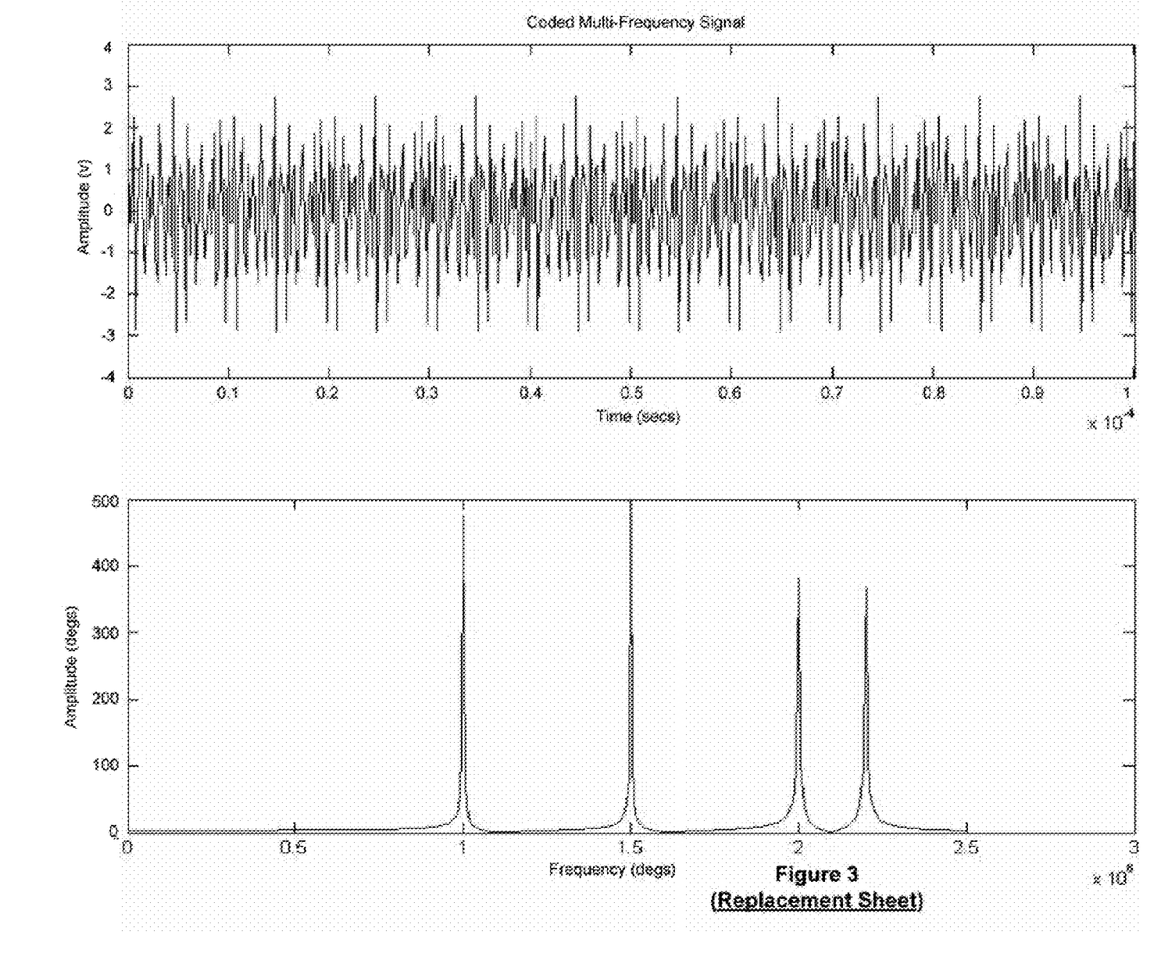
FIG. 3 is a graphs of coded multi-frequency signal.

The concept of coding multiple frequencies into a single continuous signal is based on the principle of superposition. A series of continuous signals of different frequencies can be overlaid on top of each other to create a composite signal. This composite multi-frequency signal is used to query the medium. The composite acoustic wave interacts with the matter as the superposition of the individual waves. FIG. 3 shows an example of such a signal. Here 4 frequencies are overlaid. The frequencies are 1 MHz, 1.5 MHz, 2 MHz and 2.2 MHz, all of the same amplitude. However, the relative amplitudes are of no consequence. The composite signal is shown in the top panel, and the spectrum in the lower panel. By transmitting a range of frequencies through the substance, the effects of various "colours" of the substance is investigated. This is similar to illuminating a scene with a full spectrum of light to make all colours visible. A single wideband signal can be used to effectively create the same type of multi-frequency illumination, however the single wide band signal does not allow for the beating of two frequencies as described above and, consequently, the exact travel time measurement may not be calculated.

Figure 4:
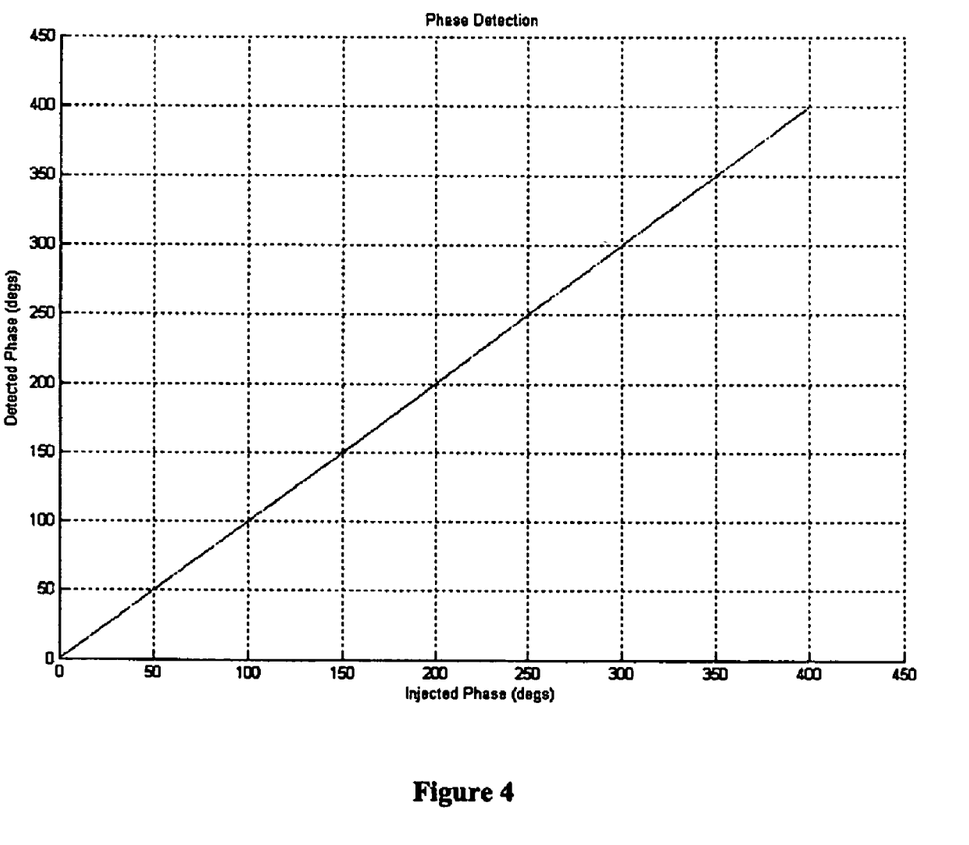
FIG. 4 is a graph of phase detection with coded multi-frequency signal.
Figure 5:
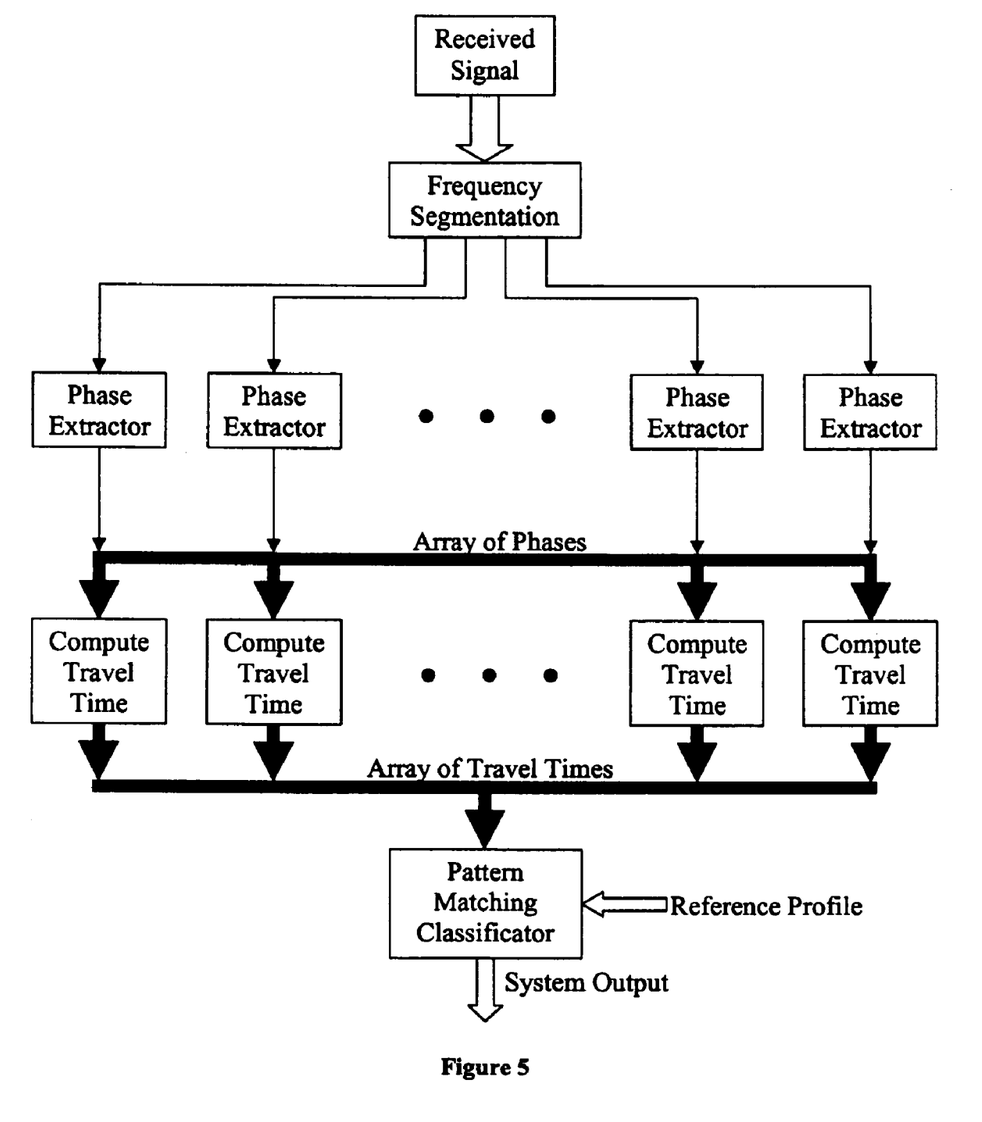
FIG. 5 is a block diagram of algorithm for determining travel time array.
Figure 6:
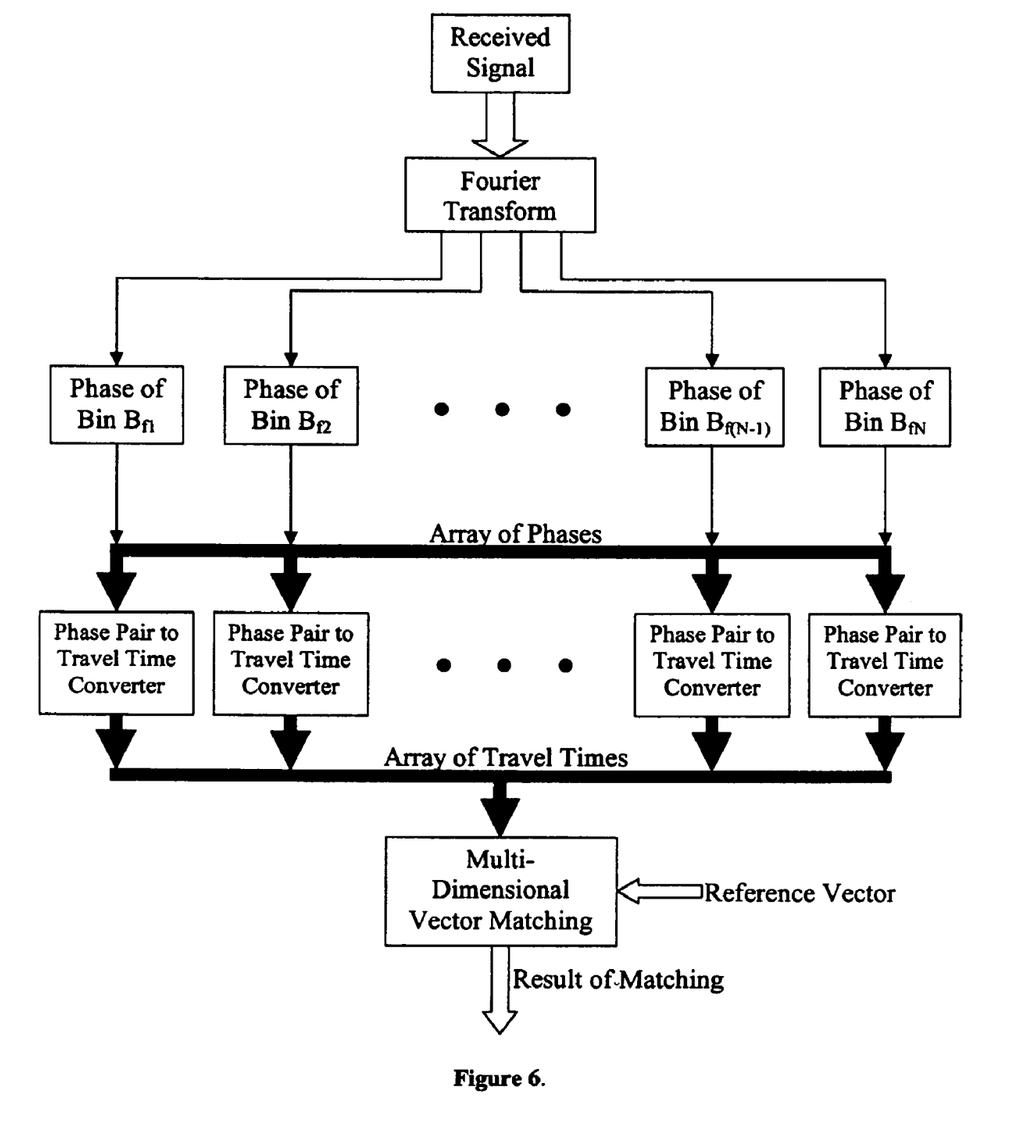
FIG. 6 is a block diagram of software implementation of algorithm for determining travel time array.
Figure 7:
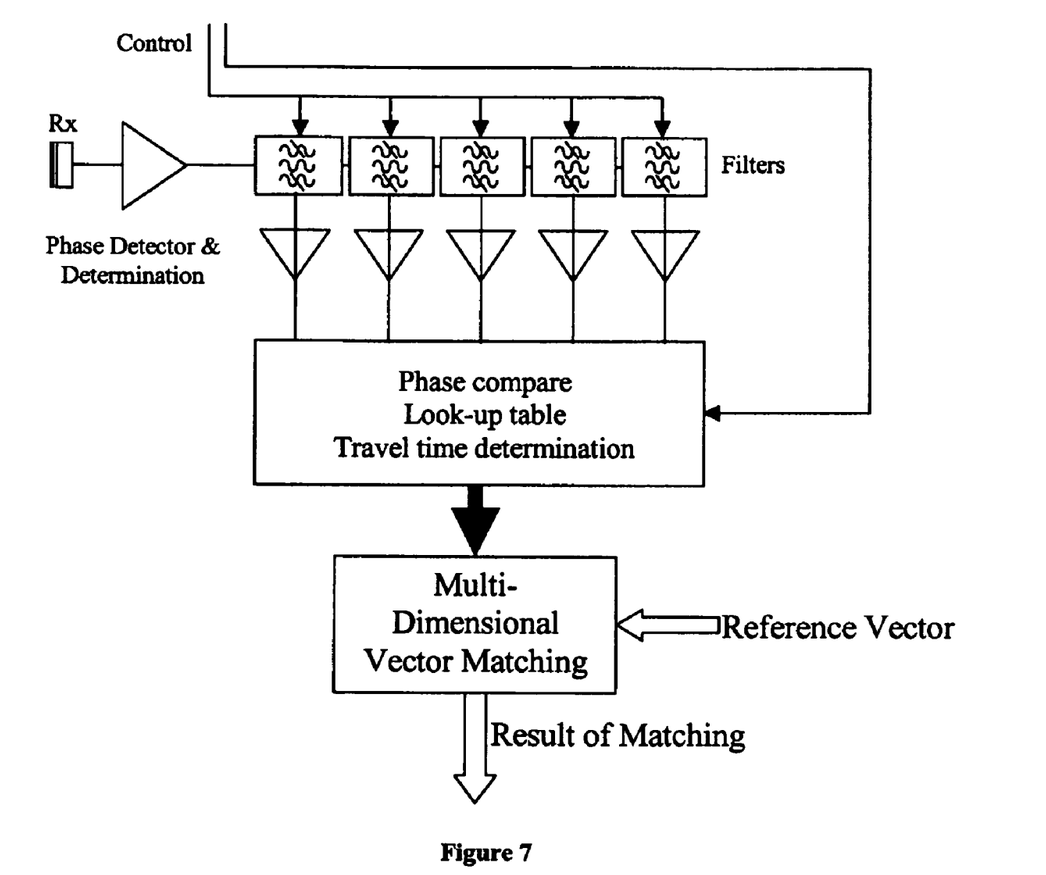
FIG. 7 is a block diagram of hardware implementation of algorithm for determining travel time array.
Figure 8:
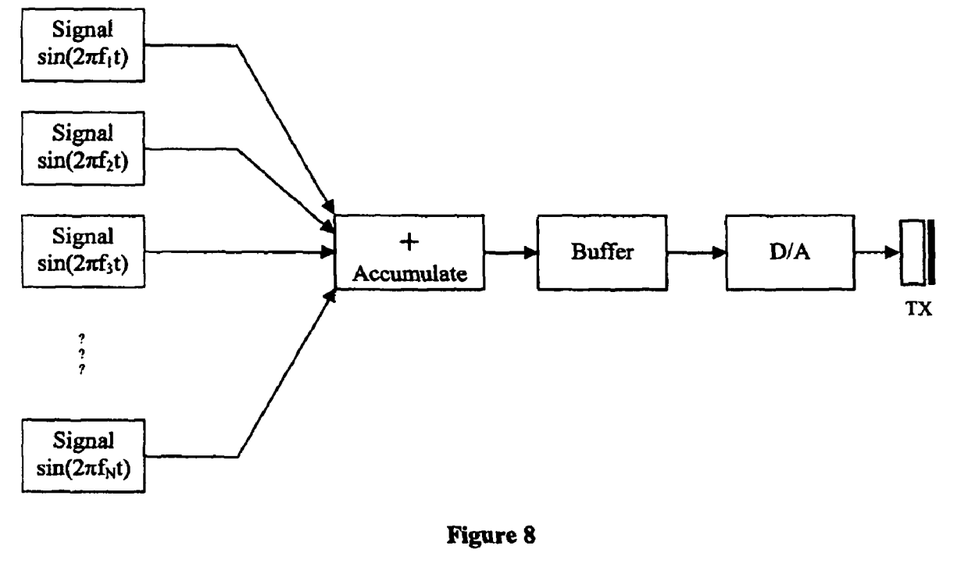
FIG. 8 is a block diagram of digital implementation of transmitting functionality.
Figure 9:
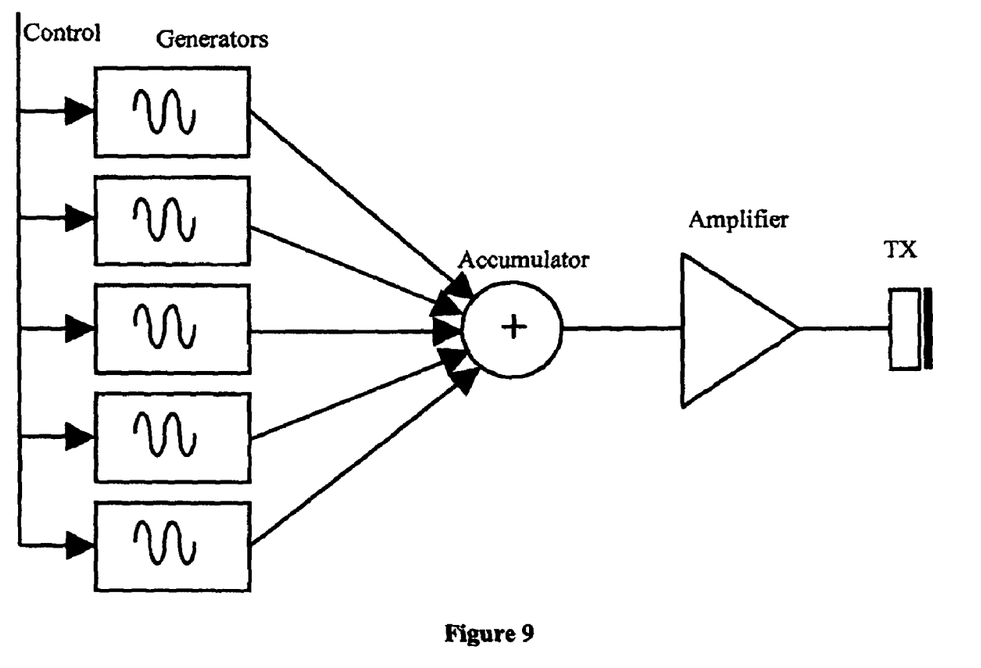
FIG. 9 is a block diagram of generic implementation of transmitting functionality; and, FIG. 10 is a block diagram of overall system.
Figure 10:
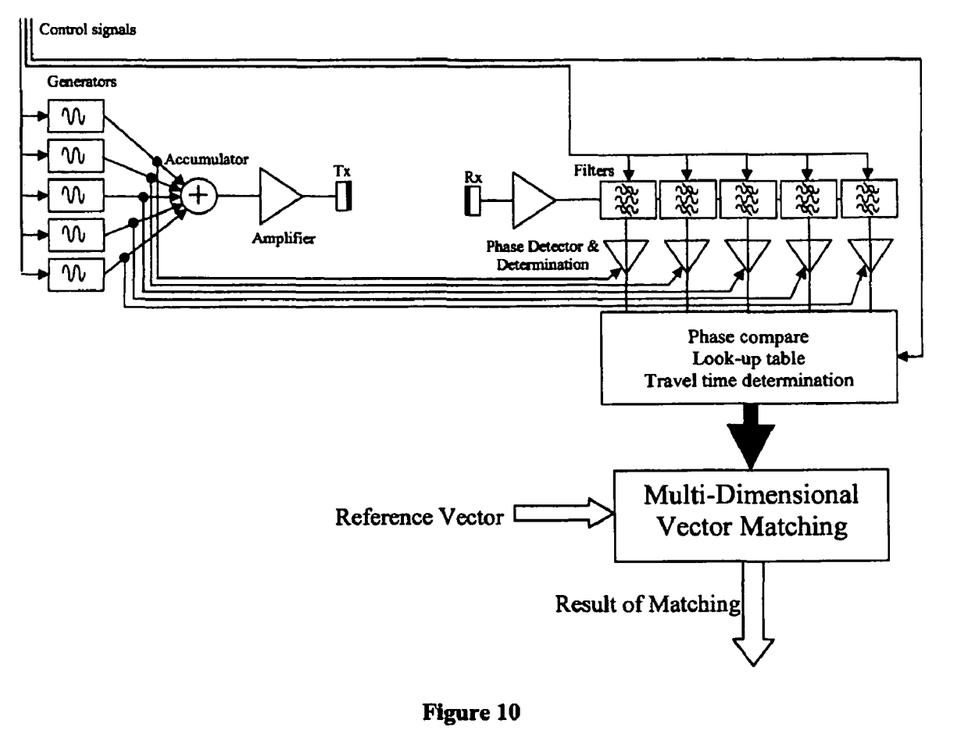

Each frequency component of this composite multi-frequency signal may be treated individually. The other 3 frequencies in this example do not have any effect on the fourth signal. FIG. 4 shows an example of the interaction of the 4 frequencies. In this example the frequency of the 2 MHz signal is changed between 0 and 400 degrees. The experiment is repeated several times, in the first experiment the phase of the 2 MHz signal is at 0 degrees, and with each subsequent experiment it is slowly increased, until it reaches 400 degrees in the last experiment. The phases of the other 3 signals are allowed to randomly vary by 10 degrees from experiment to experiment. FIG. 4 shows the measured phase of the 2 MHz signal plotted against the injected phase. It is evident here that the measured phase and the injected phases are identical. This is despite the random variations of the phases of the other 3 signals.

This frequency coding of the multi-frequency coded signal allows the system to query the medium with a large range of spectra with one transmitted wave. This is important since different frequencies interact with the material in different ways, and as a result it is necessary to query the medium with a large range of frequencies. Using the composite signal is very important for examination of a substance or a body in a chemical or bio-chemical process. In the prior art, frequencies are sent one after the other so that it requires a much longer examination time or multiple sensors in parallel. During fast processes such as the synthesis of a compound several molecules are created or destroyed at the same moment. This transition process must be measured continuously, ideally instantaneously during only one measurement cycle. A parallel sensor arrangement will meet the time requirement for fast examination, but creates a space displacement with the different detectors having different views of the space being examined. The frequency coding technique makes it possible for a simple design to be used to collect the information in the shortest possible time. The composite method based on the superposition principle allows for illuminating and measuring the characteristics with different frequencies at the same time moment.

The classification method is this patent is based on the travel time of the ultrasonic signal in the substance of interest. This travel time is directly related to the speed of sound in the particular substance. However, the speed of sound of an energy wave (ultrasound) and the attenuation of sound in the medium is not fixed, but has some frequency dependence. This frequency dependence is the basis for determining the classification of the medium, the quality of the substance or the state of the process.

The critical property of the substance in measuring this frequency dependence is the viscosity. Viscosity is the property in liquids and gases that is the cause of the dispersion of ultrasonic energy as it traverses through the medium. In solids bulk modulus is the counterpart of viscosity, and is the property of the substance that is responsible for the dispersion. The frequency dependency of the speed of sound in a medium is due to the dispersivity of the substance and this dispersivity is directly related to the viscosity of the substance (in liquids and gases) or the bulk modulus in solids. Therefore the measurement process in this invention characterizes a substance or the state of a process based on the characteristic viscosity or bulk modulus of the substance or medium. The description of the speed of sound in a medium is given by Equation 2 for solids and Equation 3 for liquids.

$$c(f) \approx \sqrt{\frac{K_B(f)}{\rho_0}} \quad (2)$$

$$c(f) \approx \sqrt{\frac{K_v(f)}{\rho_0 \beta_{ad}}} \quad (3)$$

From Equations 2 it becomes clear that the speed of sound (c) is directly linked to the bulk modulus ($K_B$) of the substance. The density ($\rho_o$) acts as a scaling factor, with no frequency dependence. Similarly Equation 3 shows that the speed of sound (c) is directly linked to viscosity ($K_V$) with the density ($\rho_o$) and the adiabatic compression ($\beta_{ad}$) acts as scaling factors. The consequence of the dispersive property of ultrasonic signals is the challenge it presents in measuring the density of a material, or medium with different frequency signals. This is because the bulk modulus of the medium as well as the density will change at the same time and the determination of the speed of sound "C" is only a rough estimate.

In the past it was believed that the dispersive effects only appeared when the energy level was sufficiently high and the dispersivity effects or the influence on the speed of sound at lower energy levels was neglected. However the dispersivity effect is present at any energy level and this patent exploits this fact. The appearance of dispersion at low energy levels may be very small and it is necessary to have the appropriate apparatus and methods to detect the minute fluctuations. The dispersive effect can be used for characterisation and classification of the substance, and that is used in this patent.

The frequencies used are spread across the spectrum. However it is necessary that at least two frequencies be chosen very close together (e.g. within approximately 0.1% of each other). The baseline density can be determined using frequencies with a long beat period. Using two sufficiently close frequencies creates this long beat period. This is also the baseline for determining the bulk modulus, which is dependent on frequency. The choice of these two frequencies close together makes the effects of the frequency dependent dispersivity negligible. For this we can say that the viscosity (dispersivity) influence is very small, smaller than may be measured in practical applications. If there are any changes in the speed of sound, then it is due to a change in density only, since the frequencies are very close together and the frequency dependency is effectively nullified. Also, these two frequencies would possess a long beat period, and using their phases the exact time of flight can be computed as previously described. Changes in this time of flight can only be as a result of a change in density, provided the relative position of the transmitter and receiver are not changed. These two waves constitute the reference travel time for this substance, and a reference of the density of the substance. Furthermore, when the substance does not have any dispersivity, all transmitted frequencies will have the same travel time through the medium as the base frequency.

However, in practice, this is not the case. Normal substances (e.g. water, milk, shampoo, human tissue) have some amount of dispersivity. This is the reason for sending frequencies that are spread across the spectrum. The higher frequencies that are used will interact with smaller molecules or cells and makes it possible to look for some specific material attributes that are directly linked to that frequency. In other words the series of frequencies can be especially chosen to monitor certain specific molecules in a material or in a process. The other frequencies are used to measure the degree of dispersivity of the substance.

An array of phase shifts are collected for all of the frequencies transmitted through the medium. This array of phase shifts is used to compute an array of frequency dependent travel times through the substance. The array of time of flight together with the reference density, is sufficient to uniquely classify the substance or the state of a process. The accurate time of flight for each frequency is computed using the base line travel time measurement together with the phase measurements across the spectrum (i.e. all of the colours of sound) to form the unique identifier of the medium. Classification of the medium means matching this identifier to a known identifier. Changes in this identifier over time provide information about changes in the density, bulk modulus, viscosity and dispersivity of the substance being examined. The time relationship of the changes can be used to identify processes taking place and used for dynamic process control. For example, the rapid increase of a time of flight at a given rate can indicate oxidization which may indicate a certain point in a larger process has been reached.

This invention pertains to the field of automated classification of a substance, or determination of the state of a process. The method uses a multi-frequency coded ultrasonic signal to query any substance that is penetrable by an ultrasonic signal (i.e. solid, liquid, or gas). By using a multi-frequency coded semi-constant wave, a large number of phase, frequency and time parameters are collected simultaneously. The phase parameters are designed to provide an immediate measurement of the exact travel time of the ultrasonic signal through the medium using a multi-spectral signal. Some of the measured phases provide a means to refine the accuracy of the time of flight measurement and create a profile of the time of flight as a function of frequency. Together all of the parameters provide the information to reliably classify the medium that was queried. The use of a wide-spectrum ultrasonic signal is analogous to illuminating a scene with white light. Various "ultrasonic colours" of the substance are investigated simultaneously.

This concludes the description of the preferred embodiment of the invention. The foregoing description has been presented for the purpose of illustration and is not intended to be exhaustive or to limit the invention to the precise form disclosed. Many modifications and variations are possible in light of the above teaching and will be apparent to those skilled in the art. It is intended the scope of the invention be limited not by this description but by the claims that follow.

What is claimed is:

1. An apparatus for investigating a characteristic of a medium, comprising: a transmitter for generating a multi-frequency coded ultrasonic signal; a receiver for receiving the signal after it has passed though the medium; a means for calculating the phase shifts of each frequency of the signal and a means for calculating an array of times of flight for the frequencies of the signal relative to a baseline established by a beat frequency resulting from two of the frequencies in the signal, wherein the array of times of flight for the frequencies identifies the characteristic of the medium.

2. The apparatus as claimed in claim 1 further comprising a means for accumulating the arrays of times of flight for the frequencies of the signal and recursively correlating the same with the characteristic of the medium.

3. The apparatus as claimed in claim 1 further comprising a library of known arrays of times of flight for frequencies and their corresponding medium characteristics; and, means for matching the measured array to a known array from the library to identify the medium characteristic.

4. The apparatus as claimed in claim 1, wherein the multi-frequency coded ultrasonic signal comprises higher frequency harmonics on a lower frequency carrier so as to enable the signal to penetrate materials impermeable to the higher frequency harmonics alone.

5. The apparatus as claimed in claim 2, wherein the multi-frequency coded ultrasonic signal comprises higher frequency harmonics on a lower frequency carrier so as to enable the signal to penetrate materials impermeable to the higher frequency harmonics alone.

6. The apparatus as claimed in claim 3, wherein the multi-frequency coded ultrasonic signal comprises higher frequency harmonics on a lower frequency carrier so as to enable the signal to penetrate materials impermeable to the higher frequency harmonics alone.

7. A method of measuring a characteristic of a medium, comprising the steps of: generating a multi-frequency coded ultrasonic signal using a transmitter; receiving the signal at a receiver after the signal has passed through the medium; calculating the phase shifts of each frequency of the signal; calculating an array of times of flight for the frequencies of the signal relative to a baseline established by a beat frequency resulting from two of the frequencies in the signal; and identifying the characteristic of the medium using the array of times of flight.

8. The method of claim 7, further comprising the steps of: accumulating the arrays of times of flight for the frequencies of the signal and recursively correlating the same with the characteristic of the medium.

9. The method of claim 8, further comprising the steps of: maintaining a library of known arrays of times of flight for frequencies and their corresponding medium characteristics; and performing the identifying step by matching the measured array to a known array from the library.

10. The method of claim 7, further including enabling the signal to penetrate materials impermeable to higher frequency harmonics alone by configuring the multi-frequency coded ultrasonic signal to comprise higher frequency harmonics on a lower frequency carrier.

11. The method of claim 8, further including enabling the signal to penetrate materials impermeable to higher frequency harmonics alone by configuring the multi-frequency coded ultrasonic signal to comprise higher frequency harmonics on a lower frequency carrier.

12. The method of claim 9, further including enabling the signal to penetrate materials impermeable to higher frequency harmonics alone by configuring the multi-frequency coded ultrasonic signal to comprise higher frequency harmonics on a lower frequency carrier.

* * * * *